Figure 7:
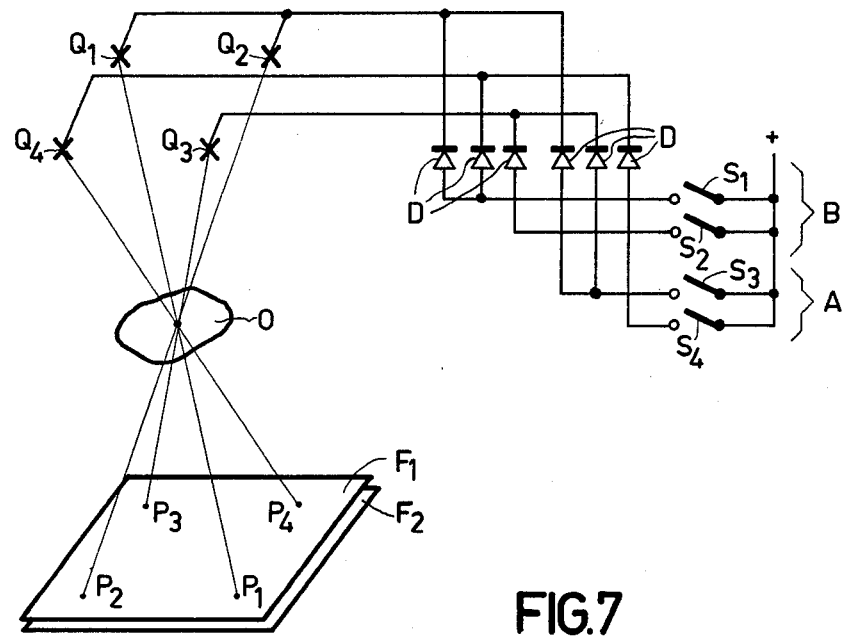

United States Patent [19]

Weiss et al.

[11] 4,404,631
[45] Sep. 13, 1983

[54] METHOD OF AND DEVICE FOR CODING AND DECODING AN IMAGE OF AN OBJECT BY MEANS OF PENETRATING RADIATION

[75] Inventors: Hermann Weiss; Klaus Pasedach, both of Hamburg, Fed. Rep. of Germany

[73] Assignee: U.S. Philips Corporation, New York, N.Y.

[21] Appl. No.: 233,616

[22] PCT Filed: Jan. 10, 1980

[86] PCT No.: PCT/NL80/00001
§ 371 Date: Jan. 21, 1981
§ 102(e) Date: Jan. 21, 1981

[87] PCT Pub. No.: WO81/01952
PCT Pub. Date: Jul. 23, 1981

[51] Int. Cl.$^3$ .................. G06F 15/336; A61B 6/02
[52] U.S. Cl. .................. 364/414; 364/728; 364/822
[58] Field of Search .......... 364/414, 728, 822

[56] References Cited

U.S. PATENT DOCUMENTS

| | | | |
|---|---|---|---|
| 4,149,259 | 4/1979 | Kowalski | 364/414 X |
| 4,212,062 | 7/1980 | Kohno et al. | 364/414 |
| 4,241,404 | 12/1980 | Lux | 364/414 |
| 4,326,252 | 4/1982 | Kohno et al. | 364/414 |

*Primary Examiner*—Jerry Smith
*Attorney, Agent, or Firm*—Jack E. Haken

[57] ABSTRACT

A method of and a device for the coding and decoding of an object by means of point-shaped radiation sources. The point sources are subdivided in groups which successively irradiate the object. Two sources distributions can be derived from the groups of radiation sources (a negative radiation intensity is assigned to at least one group), the sum of the autocorrelation functions thereof having the value "0" outside the origin. The coded images generated by means of the various groups are recorded (and also their negatives). Combinations of a coded image and a negative are decoded via point holograms or lens matrices, thus forming a subimage. The sum of all subimages forms an object image which is free of artefacts.

11 Claims, 18 Drawing Figures

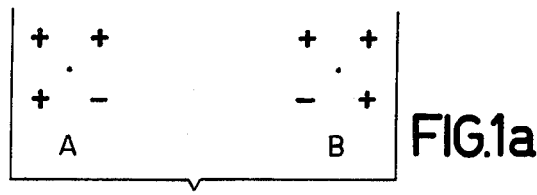
FIG.1a
FIG.1b
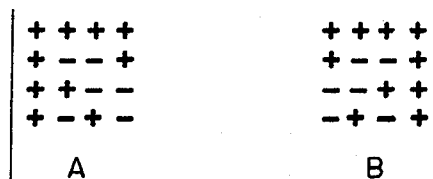
FIG.2a
FIG.2b

| A | B | n |
|---|---|---|
| + | + | 1 |
| + + | + − | 2 |
| + +<br>+ − | + +<br>− + | 4 |
| + + + +<br>+ − − + | + + − −<br>+ − + − | 8 |
| + + + +<br>+ − − +<br>+ + − −<br>+ − + − | + + + +<br>+ − − +<br>− − + +<br>− + − + | 16 |
FIG.3
```
+ + + +      + + + +
+ − − +      + − − +         n
+ + − −      − − + +        16
+ − + −      − + − +
```
↓ (5,7,3)
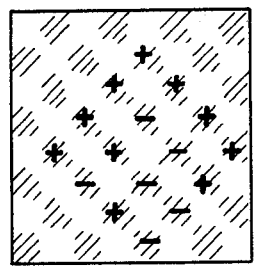 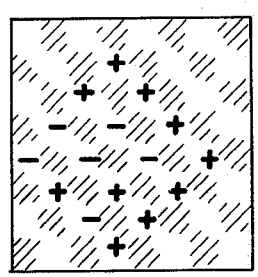
16
↓ (9)
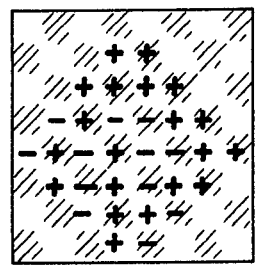 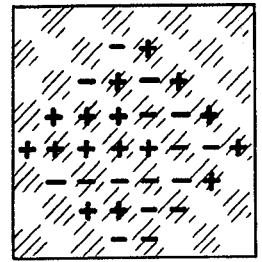
32
FIG.4

|   A   |   B   |  n  |
|-------|-------|-----|
| + + − | + · + | 3/2 |
| + + −<br>+ · + | + + −<br>− · − | 5 |
| + + −<br>+ · +<br>+ + −<br>− · − | + + −<br>+ · +<br>− · +<br>+ · + | 10 |
FIG.5
| | A | B | n |
|---|---|---|---|
| | + + − | + · + | 3/2 |
| FIG.6a |  | | 5 |
| FIG.6b |  | | 5 |
| FIG.6c |  | | 10 |
| FIG.6d |  | | 20 |
| FIG.6e |  | | |

METHOD OF AND DEVICE FOR CODING AND DECODING AN IMAGE OF AN OBJECT BY MEANS OF PENETRATING RADIATION

The invention relates to a method of coding and decoding an image of an object by means of radiation which is emitted by point sources and which irradiates the object in different directions in order to form shadow images of the object which are superposed on a recording medium, the coded image thus formed being decoded by convolution of the superposed shadow images with a function which is determined by the point source distribution used for irradiating the object.

The invention furthermore relates to a device for coding and decoding an image of an object by means of penetrating radiation, said device comprising for the coding of an image of an object a two-dimensional distribution of point sources and a two-dimensional image recording medium which are situated in two parallel planes at a distance from each other in order to form superposition images of the object, said device comprising for the decoding of the superposition images means for convoluting the recorded superposition images with at least a part of an image point function which is defined by the point source distribution, and means for summing the convoluted superposition images.

It is known that objects can be coded by irradiating the object from different positions by means of X-rays or other incoherent radiation and by recording the shadow images on a recording medium. Thus, a superposition image is obtained in which the information concerning the object is not directly accessible. The object or a layer object can be made visible again only during a second phase, i.e. the decoding of the superposition image. A method and a device of the described kind are known from German Patent Application No. P 25.35.408.9 (U.S. Pat. No. 4,118,099).

The decoding by means of the known specific arrays of the recording sources using incoherent or also coherent point distributions produces artefacts which prevent the signal-to-noise ratio from exceeding a given threshold.

The invention has for its object to provide a method of and a device for the coding and decoding of images of the described kind in which the object is decoded without disturbing artefacts.

To this end, a method in accordance with the invention is characterized in that the point sources are arranged according to a regular matrix, at least three different groups of point sources being used to form a corresponding number of superposition images in succession, a combination of groups forming a first source distribution function and a further combination of groups forming a second source distribution function, the sum of the autocorrelation functions of said source distribution functions having the value zero except in one point (origin), after which the different superposition images, or combinations with the negatives thereof, are convoluted with image point functions of the groups of sources in order to obtain convoluted images which are summed in order to obtain a decoded image. The combinations of groups which produce a first and a second source distribution function having the said property (the sum of the autocorrelation functions is zero with the exception of a value in one point (the origin)) are referred to as complementary combinations or complementary source distribution functions.

In the case of self-radiating objects, the array of radiation sources is effectively replaced by a corresponding array of diaphragms with holes wherethrough the radiation emitted by the object passes and is incident on a recording medium. The method can be used for two-dimensional as well as three-dimensional objects. In the case of three-dimensional objects, the reconstruction of the individual layers can be continuously performed by changing the scale of all superposition images on the recording means.

The artefact-free decoding of a layer may be understood to mean that the radiation sources are subdivided into groups of each time positive sources (recording on a positive film) and negative sources (recording on a negative film), so that the sum of the autocorrelation of the distributions in the origin has a high value, corresponding to the sum n of all sources, and that no secondary points occur in the sum of the autocorrelations of the two point source distributions. The decoded image is produced exactly with a mean intensity which is proportional to the value of the autocorrelation sum in the origin. It is to be noted that one-dimensional complementary codes have the arithmetical property that the sum of their autocorrelation consists of a maximum without secondary points (see IRE Transactions on Information Theory, Vol. 7, pages 82–87, 1961, M. J. E. Golay). The invention, however, is based on the use of complementary two-dimensional point codes, the two coherent codes being different and complementary in a sense that the sum of their autocorrelation has the previously described properties.

A device in accordance with the invention is characterized in that for the coding the device comprises means for the sequential activation of the point sources in at least three and at the most four different groups in order to obtain at least three coded images, a first number of groups of point sources forming a first distribution function and a second number of groups forming a second distribution function, the sum of the autocorrelations of said distribution functions having the value zero except in one point (origin), for the decoding the device comprising means for convoluting, either sequentially or simultaneously, the coded images with an image point function associated with the coded images, each of which is determined by a different group of point sources.

The decoding of the object can be performed by means of a computer, by analog electronic or by optical methods. The optical decoding can also be realized by means of a four-channel optical system, as will be described hereinafter.

The invention will be described in detail hereinafter with reference to the accompanying diagrammatic drawing.

Figure 9:
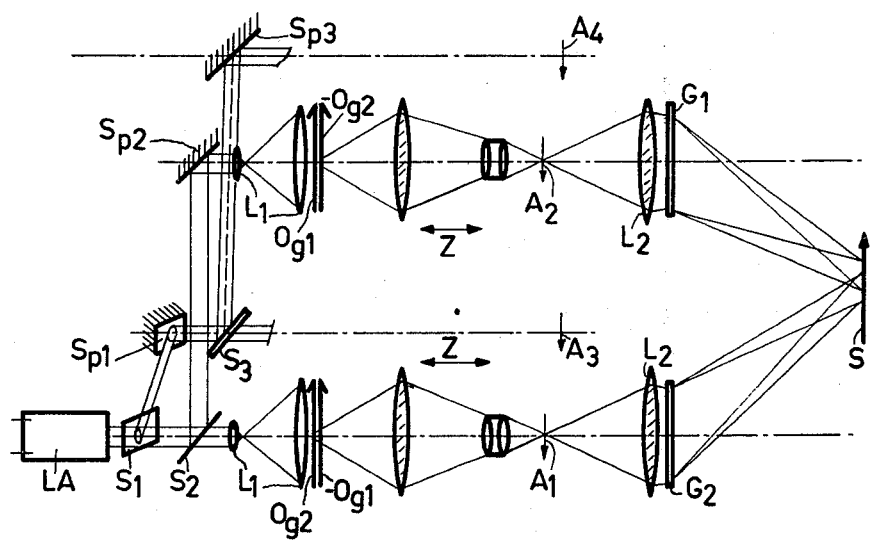
Figure 8:
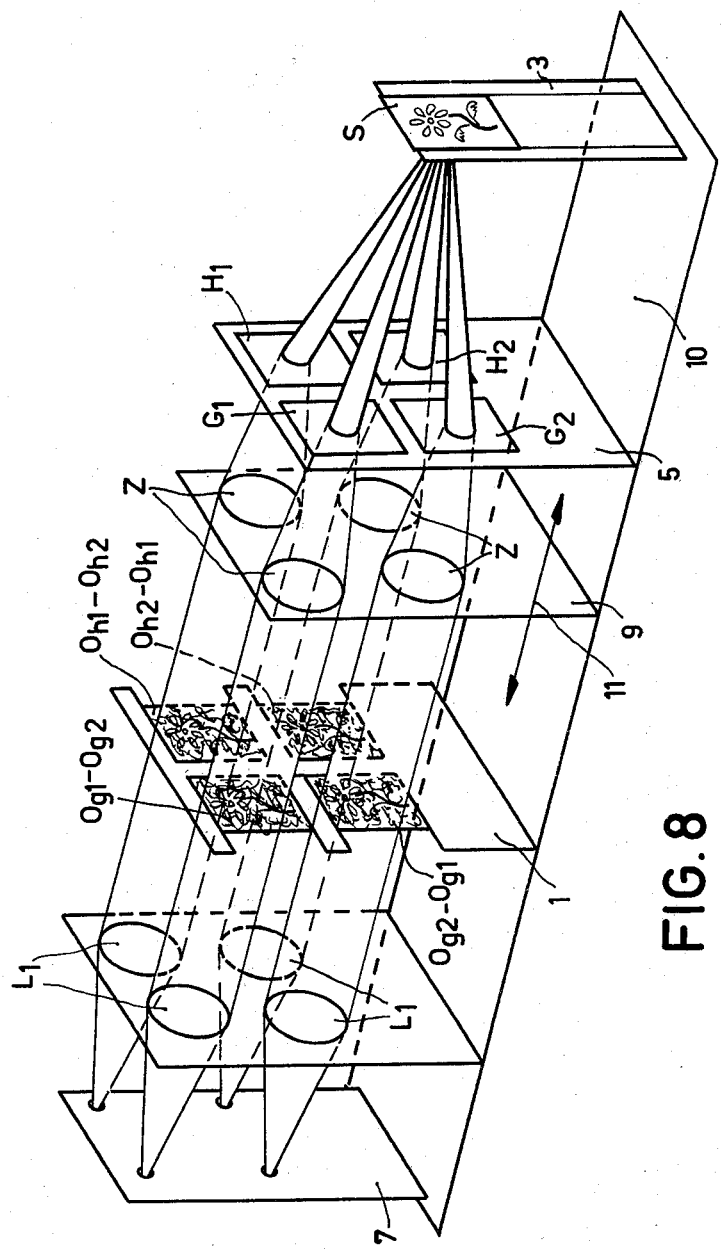
Figure 10:
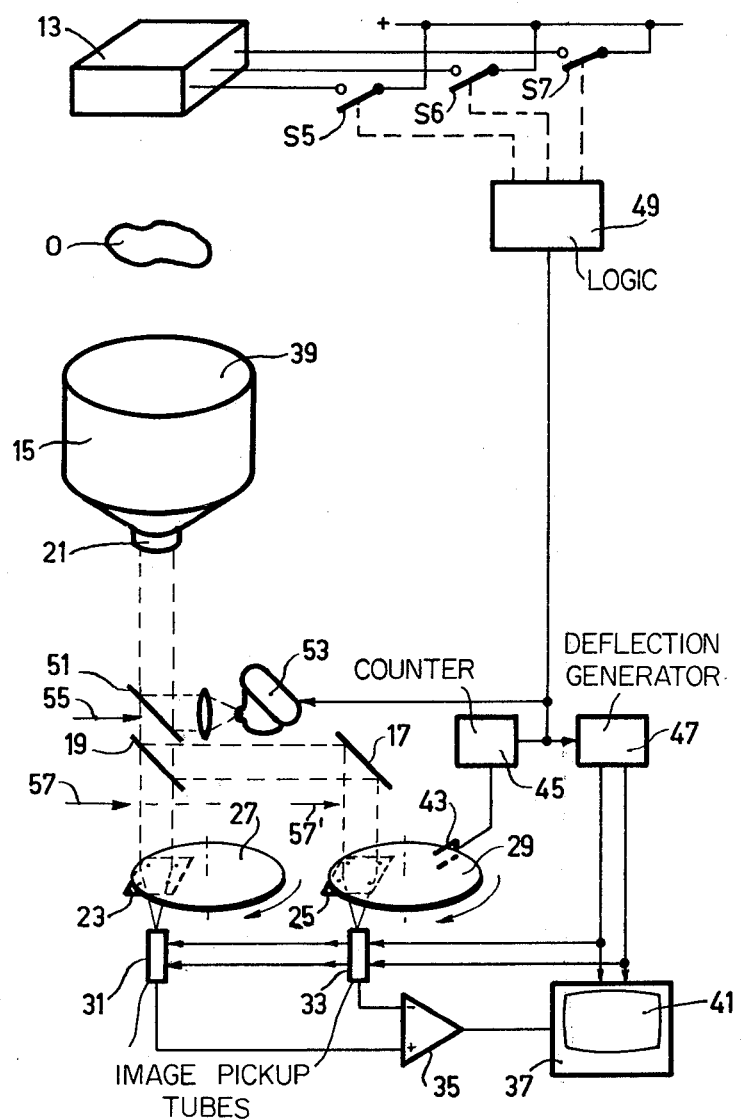
Figure 11A:
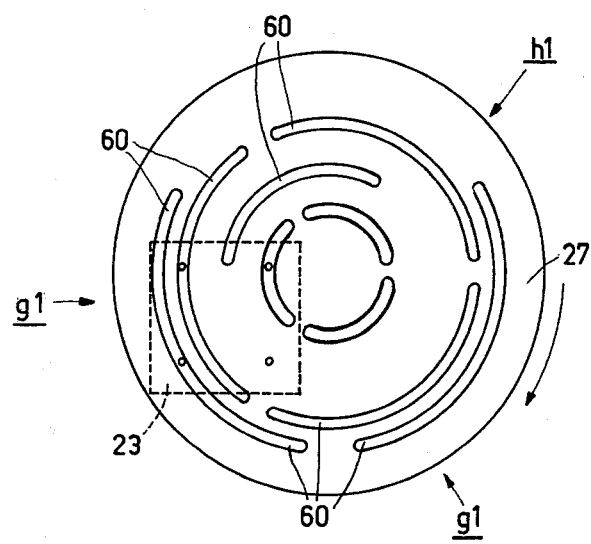
Figure 11B:
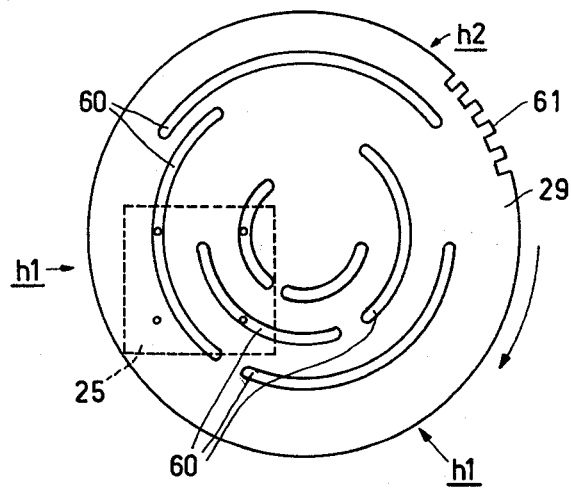

FIG. 1(a) shows complementary point codes of the order 4, FIG. 1(b) the autocorrelation of the two codes and their sum, FIGS. 2a and b show a complementary code of the order 16 and different distributions of the points in 4 groups, respectively, FIG. 3 shows complementary codes of the order n, n having the value 1, 2, 4, 8 and 16, FIG. 4 shows the combination of codes of lower order in order to form codes of higher order, FIG. 5 shows complementary codes of the order n, n having the value 3/2, 5 and 10, FIGS. 6a–d show radiation source distributions according to the complementary codes of the order n, n having the value 3/2, 5, 10 and 20, with code rotation and overlapping combination, FIG. 6e shows a slanted radiation source distribution, FIG. 7 shows an arrangement for forming coded images, FIG. 8 shows an arrangement for decoding the coded images obtained by means of the arrangement shown in FIG. 7, FIG. 9 shows a part of the optical system of the arrangement shown in FIG. 8, FIG. 10 shows an electro-optical device for the coding and the immediate decoding of a layer of the object, and FIGS. 11a and 11b are a detailed view of a part of the arrangement shown in FIG. 10.

FIG. 1 illustrates the principle on the basis of a pair of complementary point distributions (codes A, B with points + and −). An object O is recorded once by means of a point distribution with the code A, so that a coded image O′ of the object O is formed according to the correlation $$O'_A = O * A \tag{1}$$

(* means "convolution").

The object O is recorded a second time with the point source distribution B, so that the coded image:

$$O'_B = O * B \tag{2}$$

is formed.

Each of these two coded images is then subjected to a correlation with the point image distribution function A and B, respectively, resulting in $$O''_A = O * A \odot A \tag{3}$$

$$O''_B = O * B \odot B \tag{4}$$

When the images $O''_A$ and $O''_B$ thus obtained are added, the following is obtained $$O'' = O''_A + O''_B = O * (A \odot A + B \odot B) \tag{5}$$

FIG. 1b shows the autocorrelations of the point source distributions A and B and the sum of both autocorrelations. The distributions A and B are chosen so that the sum of their autocorrelation has a value only in the origin M, so arithmetically it is a δ-function, so that the equation (5) can be rewritten as:

$$O'' = O * \delta = O \tag{6}$$

Formula (6) demonstrates that the object has been faithfully reconstructed.

FIG. 2 shows an example of the coding of the object, a recording being made, for example, on X-ray film by means of X-rays.

The complementary point source distributions are of the order 16 in FIG. 2a and can be subdivided into four groups in a different manner before the recording. The distributions chosen by way of example are shown in FIG. 2b.

The distribution $P_1$ is based on the fact that each time the code point distributions A and B are separately subdivided, that is to say four recordings of the object O are made, each time with the point source distribution $g_1$, $g_2$, $h_1$ and $h_2$; $g_2$ and $h_2$ being "negative" sources. This means that the shadow images formed by means of $g_2$ and $h_2$ are subtracted from the shadow images formed by means of $g_1$ and $h_1$, respectively. Coded images according to (1) and (2) are then obtained $$O'_A = O * g_1 - O * g_2 = O_{g1} - O_{g2} \tag{7}$$

$$O'_B = O * h_1 - O * h_2 = O_{h1} - O_{h2} \tag{8}$$

in which $g_1$, $g_2$, $h_1$, $h_2$ each mark the distribution of the X-ray tubes which are simultaneously flashed.

Decoding is realized by the correlation according to (3) and (4)

$$O'' = (O_{g1} - O_{g2}) \odot (g_1 - g_2) + (O_{h1} - O_{h2}) \odot (h_1 - h_2) = \\ (O_{g1} - O_{g2}) \odot g_1 + (O_{g2} - O_{g1}) \odot g_2 + (O_{h1} - O_{h2}) \odot h_1 + \\ (O_{h2} - O_{h1}) \odot h_2 \tag{9}$$

The four additions of the equation (9) can be realized, for example, in four optical channels, as will be described hereinafter. However, from the coded image $O_{g1}$, $O_{g2}$, $O_{h1}$, $O_{h2}$ negatives also have to be made and hence the combinations $O_{g1} - O_{g2}$, $O_{g2} - O_{g1}$, $O_{h1} - O_{h2}$, $O_{h2} - O_{h1}$. The combinations are convoluted with the point distributions $g_1$, $g_2$, $h_1$, $h_2$, respectively, and are subsequently summed.

Instead of using the distribution $P_1$ during the recordings, it is alternatively possible to use the distribution $P_2$ shown in FIG. 2b. This distribution offers the advantage that it is disjunct, which means that each radiation source is used only once for the formation of coded images. The reconstruction of the object is again realized in four channels, because the distributions A and B can be composed from the distributions $t_1$, $t_2$, $s_1$, $s_2$.

Moreover, on the basis of the distribution $P_1$ of FIG. 2b, three recordings may also suffice if the complementary code pair has the property $$g_1 + g_2 3 h_1 + h_2 \tag{10}$$

which only means that the source positions of the two codes A and B correspond exactly.

It follows from (10) that:

$$h_2 = g_1 + g_2 - h_1 \tag{11}$$

so that $$O_{h2} = O_{g1} + O_{g2} - O_{h1} \tag{12}$$

Insertion of (12) in (9) produces $$O'' = (O_{g1} - O_{g2}) \odot g_1 + (O_{g2} - O_{g1}) \odot g_2 + \\ (2 \cdot O_{h1} - O_{g1} - O_{g2}) \odot h_1 + (O_{g1} + O_{g2} - 2 \cdot O_{h1}) \odot h_2 \tag{13}$$

so that only the three recordings $O_{g1}$, $O_{g2}$ and $O_{h1}$ are required. Four channels are still required for the reconstruction.

The number of channels for the reconstruction can also be reduced to three, because it also follows from (10) that $$g_2 = h_1 + h_2 - g_1 \tag{14}$$

and insertion of (14) in (13) results in $$O' = (12 \cdot O_{g1} - 2 \cdot O_{g2}) \circledast g_1 + (2 \cdot O_{h1} - 2 \cdot O_{g1}) \circledast h_1 + \qquad (15)$$
$$(2 \cdot O_{g2} - 2 \cdot O_{h1}) \circledast h_2$$

where only three recordings are made and only three channels are required for the reconstruction.

In addition to the described possibility, there are other possibilities of reducing the number of recordings and or channels for the reconstruction to three by way of (10). For example, the possibility can be chosen where in total the smallest number of sources is used for all exposures together. This is technically advantageous and it also means a lower radiation load for a patient to be irradiated.

The order of the complementary codes indicates how many X-ray tubes in a point source distribution are used for forming coded images of the object. The described method of coding and decoding is applicable to flat, two-dimensional objects. The layers of an arbitrary three-dimensional object can be decoded by changing the scale of the coded images as described in German Offenlegungsschrift No. 25.35.408.9 (U.S. Pat. No. 4,118,099).

In order to find the complementary codes, the mathematical rules for forming the compelementary codes are described hereinafter.

I. Properties of complementary codes. Some definitions.

If A is a code, $-A$ or the inverse code of A indicates the code where each $+1$ is changed into a $-1$ and vice versa. Two codes A and B are called disjunct if no position of a source of A corresponds to a position of a source of B. The sum of two disjunct codes A and B is denoted as $A+B$ and is defined as the code produced by combination of A and B. Each source in $A+B$, therefore, was already a source in A or B where it had the same value $+1$ or $-1$. The sum of two codes A and $-B$ is also indicated as the difference of A and B and is written as $A-B$.

Using these definitions, the following definitions can be demonstrated by simple algebra: Rule: When A and B are complementary codes, the following codes are also complementary:
(1) B and A.
(2) A and $-B$.
(3) A and any translation of B.
(4) A and the rotation of B through 180°.
(5) Rotations of A and B through the same angle.
(6) Mirror-images of A and B with respect to the same axis.
(7) Stretchings of A and B in the same direction and by the same factor (also $<1$ i.e. a compression)
(8) Indentical slanting of A and B.
(9) $A+B$ and $A-B$, if A and B are disjunct.

A large number of further rules can be deduced from these rules by the successive execution of some of said operations, utilizing the above rules 1 to 9.

II. Formation of complementary codes.

Using a pair of complementary codes, new complementary codes having the same source numbers can be obtained by way of the rules 1 to 8. Using the rule 9, complementary code pairs having an increasingly larger number of sources can be step-wise obtained. The formation process is in general as follows:

(a) Take an already known pair of complementary codes (for example from the one-dimensional, see FIG. 3).
(b) Apply one of the rules 1 to 8 (also several times).
(c) Apply rule 9.
(d) Terminate the formation process with the newly obtained pair or continue at (b).

An important combination is that of (b) and (c) which implies the combination of B with A and $-B$ with A, consisting of rule 3 and 9, (generalization of the one-dimensional combination which converts a pair of complementary codes A, B, each of which comprises n sources, into a new pair of complementary codes, each of which comprises 2n sources).

A further possibility is the interleaving of A and B and of A and $-B$ by way of the rule 3 (+possibly twice the rule 7) and 9.

III. Concrete codes.

Two-dimensional complementary codes can be obtained in accordance with the combination of rules (under II) as follows: Use is made of the codes A and B, each of which consists of only one source $+1$. First a horizontal combination of B with A and $-B$ and A is performed, the codes thus produced being renamed A and B. Subsequently, a similar vertical combination is performed, followed by a horizontal combination etc. Thus, for each integer n a pair of complementary codes of the order $2^n$ is obtained and for each even n even source distributions which exactly form a square having the length and the width $2^{n/2}$. The first five pairs of complementary codes obtained according to this rule are shown in FIG. 3.

IV. Invariability of complementary codes.

The codes given in III and in FIG. 3 represent only some examples for complementary pairs. Obviously, as is indicated sub II, complementary codes can also be derived from the rules given sub I in many other ways, notably by rotation, mirror-imaging stretching and slanting of the codes given in FIG. 3.

The codes given therein, whose order is an odd power of 2 (2, 8, ...) have a rectangular shape instead of a square shape, the length of said rectangle being twice its width. However, using the general formation rule stated sub II, codes with a distribution in an approximately square area can also be indicated for these orders.

To this end, it is ensured by rotation through 45° (rule 5) and stretching by the factor 2 (rule 7) that two complementary codes occupy exactly the black fields of an (imaginary) checkerboard (FIG. 4). Translation in the horizontal direction by one field to the left (rule 3) ensures that the first code occupies the black fields of the checkerboard and the second code occupies the white fields. Subsequently, the two codes are interleaved in accordance with rule 9, as described sub II.

When the codes used as a basis define a source distribution in a square area, such a distribution will also be defined by the codes produced by interleaving (in any case, the square is rotated through 45°). In FIG. 4 this principle for converting the described complementary code pair of the order 16 into a code pair of the order 32, which defines a source distribution in an almost square area, has been shown.

Using the same combination principle previously used for forming the complementary codes of the orders 1, 2, 4, 8, 16, new complementary code pairs can also be obtained, starting also with a different complementary pair of codes, and the positioning of the radiation sources for the image coding can be defined accordingly.

Hereinafter it is shown, by way of example (FIG. 5), how from the pair of codes $$+ + - \text{ and } + \cdot +$$

determined directly as a complementary pair and one of which has the order 3 and the other has the order 2, a series of complementary code pairs of the orders 5, 10, ... are built up. The combination is not always performed alternately vertically and horizontally, but such that always a source distribution in a square area is defined as well as possible.

The FIGS. 6a-d show radiation source distributions for codes of the order 3/2, 5, 10, 20, utilizing the combination rule (1) (FIG. 6b), the rotation rule (4) (FIG. 6c), and overlapping combinations (FIG. 6d) being used. FIG. 6e shows a regular matrix structure of equilateral triangles obtained by slanting through 30° to the left.

The arrangement shown in FIG. 7 comprises four X-ray sources $Q_1$ to $Q_4$ which are arranged in one plane and which can be connected to a power supply + via diodes D and switches $S_1$ to $S_4$. When the switches $S_1$ to $S_4$ are operated, part of the sources $Q_1$ to $Q_4$ irradiate an object O, so that shadow images of the object O are formed on a positive film $F_1$ and a negative film $F_2$. For the sake of clarity, these shadow images are not shown. The two films $F_1$ and $F_2$ are arranged parallel to the plane in which the sources Q are arranged. The arrangement shown in FIG. 7 corresponds to the radiation (point) source distribution shown in FIG. 1. The radiation sources to be activated via the switches $S_1$ and $S_2$ form a code B. The radiation sources to be activated via the switches $S_3$ and $S_4$ form a code A. When the switch $S_1$ is closed for a brief period of time T, the object O is irradiated by the sources $Q_1$, $Q_2$ and $Q_4$. As described with reference to FIG. 2, the coded images $O_{g1}$ and $-O_{g1}$ are recorded on the films $F_1$ and $F_2$. After replacement of the films $F_1$ and $F_2$, the switch $S_2$ is closed for the same period of time T, so that $O_{g2}$ and $-O_{g2}$ are recorded. Subsequently, the coded images $O_{h1}$ and $-O_{h1}$ and $O_{h2}$ and $-O_{h2}$, respectively, are recorded by the closing and opening of the switches $S_3$ and $S_4$ respectively.

The coded images $O_{g1}$, $-O_{g1}$, ... $O_{h2}$ and $-O_{h2}$, obtained by means of the arrangement described with reference to FIG. 7, are decoded by means of an arrangement which will be described with reference to FIG. 8. The arrangement shown comprises four optical channels, each of which is irradiated by one of four parallel beams of monochromatic light. The four light beams can be obtained, for example, by the splitting of a laser beam LA by means of semitransparent and fully reflective mirrors (see FIG. 9). Each processing channel comprises a first lens system L1 for forming a wide light beam from the narrow laser beam in order to illuminate the coded images $O_{g1}$ to $-O_{h2}$. The light beams modulated by the coded images are projected on point holograms H, G via zoom lenses Z. Behind the point holograms $H_1$, $H_2$, $G_1$, $G_2$ there is arranged a projection screen S on which four light beams from the point holograms form a decoded image. The decoded image is an image of section of the object O (see FIG. 7), said section being situated parallel to the plane in which the sources $Q_1$ to $Q_4$ are situated.

As will be clear from the formula (9), in the first channel the decoded (positive) image $O_{g1}$ and the negative of the coded image $O_{g2}$ are arranged. Using the point hologram $G_1$ of $g_1$, the sum of the two coded images $O_{g1}$ and $-O_{g2}$ is decoded. In the second channel there are situated the coded (positive) image $O_{g2}$ and the negative $O_{g1}$ which are decoded together with the point hologram $G_2$ of $g_2$. In the third channel there are situated the coded image $O_{h1}$, the negative of the image $O_{h2}$ and behind the zoom lens the point hologram $H_1$. Obviously, in the fourth channel there are situated the coded image $O_{h2}$ and the negative of $O_{h1}$ which are decoded via the point hologram $H_2$. The coded images $O_{g1}$ to $O_{h2}$ and the negatives thereof are pair-wire slid on a frame 10 which is arranged on a rigid support 1, which may be a slide frame holder. Similarly, there is provided a second frame 3 in which a (photo)sensitive film can be inserted for the recording of a decoded image. The lens system L1 and the point holograms $G_1$, $H_1$, $G_2$ and $H_2$ are each secured in a stationary frame 7 and 5, respectively, and require only one optical alignment operation, together with the zoom lens Z which are mounted in a frame 9 which is displaceable parallel to the optical axis (direction indicated by arrows 11) of each channel for reasons yet to be described. The arrangement briefly described above can be constructed by means of conventional optical means such as mirrors, lenses, lens holders, and other customarily used parts.

FIG. 9 is a more detailed view of two optical channels of the arrangement of FIG. 8. A laser LA is used to form a monochromatic light beam which is split into two parallel light beams by the mirrors $S_1$ and $Sp_1$. Each beam in its turn is split into two further parallel beams, so that four parallel light beams are formed due to the use of the mirrors $Sp_2$ and $Sp_3$ and the semitransparent mirrors $S_2$ and $S_3$. The light beam is converted in each optical channel by a lens system $L_1$ into a wide beam of light which illuminates the entire coded image (for example, $O_{g1}$ and $-O_{g2}$). Instead of the large lens of the lens system L1, use can alternatively be made of a frosted glass plate, the distance between the frosted glass plate and the coded images being as small as possible. The light transmitted by the coded image is converted, via a zoom lens system Z, into an intermediate image $A_1$, $A_2$, $A_3$, $A_4$ which is decoded via the imaging lens $L_2$ and the hologram $G_1$, $G_2$. The decoded image obtained via a channel is a sub-image which forms a complete (decoded) image S in conjunction with the three sub-images obtained via the further optical channels. Instead of using the imaging lens and the hologram (the point hologram or the multiplication hologram is the image point function of the group of sources with which the coded positive image arranged in the optical channel is formed), use can be made of a matrix of lenses, the position of the lenses in the matrix being determined by the image point function (the positions of the X-ray sources used for the recording).

It is to be noted that an arrangement for the decoding of coded images which comprises only two optical channels is already known from the German Offenlegungsschrift No. P 25.35.408.9 (U.S. Pat. No. 4,118,099).

FIG. 10 shows a device for the coding of images and the decoding of coded images. The device comprises a holder 13 in which there are arranged a number of X-ray sources, an image intensifier 15, two decoding sections which are coupled to the exit window 21 of the intensifier via a fully reflective mirror 17 and a semitransparent mirror 19, each of said decoding sections comprising a lens matrix 23, 25, a diaphragm 27, 29, an image pick-up tube 31, 33, a differential amplifier 35, and an image display device 37 in the form of a television monitor.

The X-ray tubes arranged in the holder 13 are subdivided into three sub-groups, each of which can be connected to the power supply voltage + via an associated switch $S_5$, $S_6$, $S_7$. The sub-division into three subgroups is realized on the basis of the rule described with reference to FIG. 2b ($P_1$). The switches $S_5$, $S_6$, $S_7$ are sequentially closed and opened, so that the coded images $O_{g1}$, $O_{g2}$ and $O_{h1}$ of an object are projected onto the entrance screen 39 of the image intensifier 15 sequentially with the subgroups. The image received by the image intensifier is displayed on the exit screen 21 in reduced and intensified form. Via the semitransparent mirror 19, the coded image $O_{g1}$, $O_{g2}$ or $O_{h1}$, is projected onto a rotating diaphragm 27. The diaphragm 27 leaves given parts of the lens matrix uncovered, as will be described hereinafter, so that the coded images $O_{g1}$, $O_{g2}$ and $O_{h1}$ are decoded with the image point functions $g_1$, $h_2$, and $h_1$, respectively. The decoded images are picked-up by the image pick-up tube 31.

The decoding of the images $O_{g1}$, $O_{g2}$ and $O_{h1}$ with the correct image point function $g_1$, $h_2$ and $h_1$ is realized as follows (FIGS. 11a and 11b). Each of the diaphragms 27 and 29 comprises three sectors. Each sector comprises slots 60 which enable the passage of the light to given lenses of the lens matrix in a given position of the diaphragm. The cooperation between the switches $S_5$, $S_6$, $S_7$, the diaphragms 27, 29 and the shape of the diaphragms will be described, by way of example, with reference to the source arrangement shown in FIG. 7. As can be seen in formula (15), an image of a section of an object is objected by a sum of three correlations. The formula 15 can be rewritten as:

$$O'' = 2 \cdot (O_{g1} \circledast g_1 - O_{g1} \circledast h_1) + \\ 2 \cdot (O_{h1} \circledast h_1 - O_{h1} \circledast h_2) + \\ 2 \cdot (O_{g2} \circledast h_2 - O_{g2} \circledast g_1) \quad (15')$$

When the object is exposed by means of the sources $Q_1$, $Q_2$ and $Q_4$ (subgroup with the image point function $g_1$) during a first exposure operation, the coded image $O_{g1}$ (appearing on the exit window 21 of the image intensifier 15) is decoded with the function $g_1$ via the semitransparent mirror 19, the diaphragm 27 and the lens matrix 23. To this end, the diaphragm 27 comprises slits in a sector (see FIGS. 11a and b) which leave the location of the lenses in the matrix free during a third of the revolution of the diaphragm 27. Via the semitransparent mirror 19, the mirror 17, the diaphragm 29 and the lens matrix 25, the coded image $O_{g1}$ is also decoded with the function $h_1$ (see FIGS. 11a and b). The decoded images are picked-up by means of the pick-up tubes 31 and 33 and are converted into an electric signal. The two electric signals thus obtained are applied to a differential amplifier 35, the output signal of which is applied to the monitor 37, so that the difference between the two signals: $2.(O_{g1} \circledast g_1 - O_{g1} \circledast h_1)$ is displayed on a screen 41.

For a second exposure of the object, the sources $Q_1$, $Q_2$ and $Q_3$ are used. The coded image $O_{h1}$ obtained via the image intensifier 15 is processed in the same way as the previously coded image $O_{g1}$. The diaphragm 27 and 29, however, have been rotated one third of a revolution further, so that the coded image $O_{h1}$ is decoded with the function $h_1$ via the diaphragm 27 and with the function $h_2$ via diaphragm 29. The decoded images are applied to the monitor via the pick-up tubes 31, 33 and the differential amplifier circuit 35 (the applied signal: $2.(O_{h1} \circledast h_1 - O_{h1} \circledast h_2)$.

For a third exposure of the object, only a single source $Q_4$ is used. Like the two previously coded images $O_{g1}$ and $O_{h1}$, the coded image $O_{g2}$ is decoded via the lens matrices 23 and 25 and the diaphragms 27 and 29. The diaphragms are rotated a third of a revolution further against with respect to their position during the second exposure, so that now the coded image $O_{g2}$ is decoded, via the diaphragm 27, with the function $g_1$ and the coded image $O_{g2}$ is decoded with the function $h_2$ via the diaphragm 29. The decoded images are applied to the monitor 37 via the pick-up tubes and the differential amplifier circuit 35. The applied signal $2.(O_{g2} \circledast g_1 - O_{g2} \circledast h_2)$ $(=2.(O_{g2} \circledast h_2 - O_{g2} \circledast g_1))$ has changed its sign, because the source $Q_4$ used is a "positive" source, whilst according to the calculation a "negative" source has to be used (which actually does not exist).

The third exposure is followed again by an exposure by means of the first group of X-ray sources $Q_1$, $Q_2$ and $Q_4$, for which the diaphragms 27 and 29 are rotated one third of a revolution further, i.e. back to their starting position. After the repeat of the first exposure, the second and the third irradiation are repeated etc.

If the image frequency (exposure frequency) is high enough, the successive images on the monitor screen will be observed as one image due to the inertia of the human eye. The use of an image screen with some after glow will also stimulate the "summing" of the successive images.

In order to synchronize the (continuous) rotation of the diaphragms with the exposure of the object and the reading of the pick-up tubes, near a diaphragm 29 there is arranged an optical detector 43 which per second supplies a number of pulses which are a measure for the (rotary) position of the diaphragms which are driven together (not shown). A pulse divider 45, used as a counter, counts the number of pulses and supplies a pulse when a given position is reached. Via the control logic 49, whereto the pulse is applied, a switch $S_5$, $S_6$ or $S_7$ is briefly closed for a next exposure. The pulse is also applied to a deflection signal generator 47 in order to synchronize the reading of the two image pick-up tubes 31 and 33 and the display of the images read with the speed of revolution of the diaphragms.

Instead of using synchronously rotating diaphragms, use can also be made of stationary diaphragms, in which case electromechanical shutters are used for blocking the passage of light to a lens of the lens matrix or not. The opening and closing of the shutters should then be synchronized, like the opening and closing of the switches $S_5$, $S_6$, $S_7$, for the successive exposures by means of the deflection signals (for example, for the monitor). Via a semitransparent mirror 51, the coded images successively formed on the exit screen 21 can be recorded by means of a film camera 53, a film image being made of each object image. To this end, the film camera 53 is coupled to the pulse divider 45 for the required synchronization pulse.

A film thus exposed can be introduced into the decoding array again (after development) by projecting the film against the rear of the mirror 51 as indicated by an arrow 55. As a result, a moving object can be studied, without it being necessary to expose this object each time to X-rays again.

Furthermore, between the mirrors 23 and 25 and the diaphragms 27 and 29 two coupled zoom lenses can be arranged (denoted by arrows 57 and 57') in order to enable reconstruction of more than one layer of the object, as shown in FIG. 9. For the sake of clarity, the zoom lenses are not shown in the Figure.

The diaphragms used in the device shown in FIG. 10 are shown in the FIGS. 11a and b. Each diaphragm 27, 29 is formed by a round disc, for example, of aluminium which is divided into three sectors, in which some slits 60 which are shaped as an arc of a circle are provided. The slits 60 in each sector allow the passage of the light originating from the exit window of the image intensifier to some of the lenses in the matrix 23, 25 arranged behind the diaphragm (diagrammatically shown). Thus, during rotation of the diaphragms 27, 29, the coded image is decoded with a function which is determined by the sector of the disc which is situated in front of the lens matrix. As appears from the foregoing description, the diaphragm 27 should comprise three sectors which produce the functions $g_1$, $h_1$ and $g_1$ in conjunction with the lens matrix 23. The diaphragm 29 should comprise three sectors which produce the functions $h_1$, $h_2$ and $h_1$ in conjunction with the lens matrix 25. The edge of the disc is provided with slits 61 (only a few are shown) which produce pulses in conjunction with an optical sensor (FIG. 10).

What is claimed is:

1. In a method for coding and decoding an image of an object which comprises the steps of: forming superposed, coded shadow images of the object by irradiating the object with radiation emitted in different directions from point sources of radiation, recording the superposed images on a recording medium, and subsequently decoding the coded images formed by convolving of the superposed shadow images with a function which is representative of the distribution of the point sources used to irradiate the object; the improvement wherein:

the step of irradiating the object comprises irradiating the object with radiation which is emitted from point sources which are distributed in a regular matrix and are divided into at least three groups so that the position of the sources in a first combination of the groups is described by a first source distribution function and the position of the sources in a further combination of the groups is described by a second source distribution function and the sum of the autocorrelation functions of the first and second source distribution functions has a nonzero value at a single point and a zero value at all other points;

the step of forming the coded images includes successively activating each of the groups of point sources to form a corresponding number of successive superposition images and the step of decoding includes the steps of convolving positives and/or negatives of the superposition images, with point image functions of the groups of sources to form convoluted images; and summing the convoluted images to produce a decoded image.

2. A mwethod as claimed in claim 1 wherein:

the coded shadow images are formed by successively activating the point sources in four disjunct groups, the positions of sources in the groups being characterized by a first source distribution function and a second source distribution function and the shadow images are decoded by associating the coded images formed by the groups of sources with the distribution functions so that a positive of a first coded image formed by a first group of sources is used with both the first distribution function and with the second distribution functions, a negative of a second coded image formed by a second group of sources is used with the first distribution function and with the second distribution function, a positive of a third coded image formed by a third group of sources is used with the first distribution function and a negative of the third coded image is used with the second distribution function, a negative of a fourth coded image formed by a fourth group of sources is used with the first distribution function and a positive of the fourth coded image is used with the second distribution function;

forming a first sum of the positives of the first and third coded images and the negatives of the second and fourth coded images and convolving the first sum with the point image function of the first group of sources to produce a first sub-image;

forming a second sum of the negative of the first coded image with the positive of the second coded image and convolving the second sum with the point image function of the second group of sources to form a second sub-image;

forming a third sum of the positive of the third coded image with the negative of the fourth coded image and convolving the third sum with the point image function of the third group of sources to form a third sub-image; and forming a fourth sum of the negative of the third coded image with the positive of the fourth coded image and convolving the fourth sum with the point image function of the fourth group of sources to form a fourth sub-image; and summing the first, second, third, and fourth sub-images to produce a decoded image of the object.

3. A method as claimed in claim 1 wherein each source distribution function describes the position of all of the sources used to irradiate the object comprising, dividing all of the sources into a first group and a second group which are associated with the first source distribution function and further dividing all of the sources into a third group and a fourth group which are associated with the second source distribution function;

wherein the step of forming the coded images comprises irradiating the object with the first group of sources, the second group of sources, and with an additional group of sources which is either the third group or the fourth group and wherein the step of recording includes recording both positive and negative forms of each of the coded images thus produced.

4. A method as claimed in claim 3 wherein the step of decoding comprises:

forming a first sum of the positive of one of the images coded with the first and second groups of sources and the negative of the other image coded with the first and second groups and convolving that first sum with the point image function of the first group to form a first sub-image;

convolving the negative of the first sum with the point image function of the second group to form a second sub-image;

forming a second sum by doubling a positive of the image coded with the additional group of sources and the negatives of the images coded with the first and second groups and convolving the second sum with the point image function of the additional groups of sources to form a third sub-image;

convolving the second sum with a point image function which is determined by the difference between the point image function of all of the sources and the point image function of the additional group to form a fourth sub-image; and summing the first, second, third, and fourth sub-images to produce a decoded image of the object.

5. A method as claimed in claim 3 wherein the steps of convolving and summing comprise:

forming a first sum from the positive of the image coded with the first group of sources and the negative of the image coded with the second group of sources and convolving the first sum with the point image function of the first group to form a first sub-image;

forming a second sum from the positive of the image coded with the additional group and the negative of the image coded with the first group and convolving the second sum with the point image function of the additional group to form a second sub-image;

forming a third sum from the positive of the images coded with the second group and the negative of the image coded with the additional group to form a third sum and convolving the third sum with the difference between the point image function of all sources and the point image function of the additional group to form a third sub-image; and producing a decoded image by summing the first, second, and third sub-images.

6. A method as claimed in claim 3 wherein the decoding comprises the sequential steps of:

simultaneously convolving an image coded by means of the first group of sources with the point image function of the first group and with the point image function of the third group of sources to obtain first and second sub-images, respectively, and subtracting the second sub-image from the first sub-image to obtain a first difference image;

separately and simultaneously convolving an image coded by means of the third group of sources with the point image functions of the third and fourth groups of sources to obtain third and fourth sub-images respectively and subtracting the fourth sub-image from the third sub-image to obtain a second difference image;

separately and simultaneously convolving an image coded by means of the second group of sources with the point image functions of the first and fourth group of sources to respectively obtain a fifth and sixth sub-image and subtracting the sixth sub-image from the fifth sub-image to obtain a third difference image; and summing the first, second, and third, difference images to produce a decoded image.

7. A device for coding and decoding an image of an object by means of penetrating radiation comprising: a two dimensional, planar distribution of point sources of penetrating radiation; a two dimensional recording medium disposed in a plane parallel to the plane of the radiation sources; the object being disposed between the sources and the recording medium; and means for decoding superposition images formed on the recording medium by convolving the superposition images with at least a part of a point image function which corresponds to the two dimensional distribution of sources and summing the convoluted superposition images; wherein, as an improvement:

the device further includes means for sequentially activating the point sources in at least three and at most four different groups to obtain at least three distinct coded superposition images;

the positions of a first number of the groups of point sources define a first source distribution function and the positions of a second number of groups of point sources define a second source distribution function;

the sum of the autocorrelation of the first and second distribution functions has a nonzero value at a single point and a zero value at all other points; and the means for decoding comprises means for convolving each of the coded images with an associated point image function which is defined by the positions of point sources in the associated group of sources.

8. A device as claimed in claim 7 wherein the means for decoding the coded images comprises:

at least three parallel, processing channels; each channel comprising means for creating a flat, two dimensional difuse light source, a holder for at least one coded image disposed in the path of the light source, a lens, and a point hologram of the point source distribution associated with the coded image; and a projection screen;

the means for creating a light source, holder, lens, and point hologram in each channel being disposed to form a sub-image on the projection screen.

9. A device as claimed in claim 7 wherein the means for decoding the coded images comprises at least three parallel, processing channels; each channel comprising means for creating a flat two dimensional diffuse light source, a holder for at least one coded image disposed in the path of the light source, and a matrix of lens wherein the position of which lenses in the matrix is determined by the point source distribution associated with the coded image; and a projection screen;

each of the channels being disposed to project a sub-image on the screen via its lens matrix.

10. A device as claimed in claim 7 wherein the means for decoding comprises:

radiation detector means for forming a two dimensional luminescent coded image on an output thereof;

means for forming two identical luminescent coded images from the single image on the output of the radiation detector means;

two separate matrixes of lenses and a variable diaphram for forming two separate optical convolutions of the two luminescent images with respective point image functions which are associated with the two images, the position of the lenses in the matrixes being determined by the positions of the point sources in the point source distributions;

two image pickup means having targets disposed, respectively, to receive the convolutions for electrically scanning the convolutions;

differential stage means connected for receiving outputs from the image pickup means and for forming a difference therebetween and;

display means connected to an output of the differential stage means for displaying the difference;

and the device further comprises means for sequential activation of three groups of point sources and for changing the geometry of the variable diaphram to a different configuration when each of the three groups of sources is activated.

11. A device as claimed in claim 7 wherein the means for decoding comprises:

radiation detector means for forming a two dimensional luminescent coded image on an output thereof;

means for forming two identical luminescent coded images from the single image on the output of the radiation detector means;

two separate matrixes of lenses and a variable diaphram for forming two separate optical convolutions of the two luminescent images with respective point image functions which are associated with the two images, the position of the lenses in the matrixes being determined by the positions of the point sources in the point source distributions, two image pickup means having targets disposed, respectively, to receive the convolutions for electrically scanning the convolutions;

differential stage means connected for receiving outputs from the image pickup means and for forming a difference therebetween and;

recording means connected to an output of the differential stage means for recording the difference;

and the device further comprises means for sequential activation of three groups of point sources and for changing the geometry of the variable diaphram to a different configuration when each of the three groups of sources is activated.

* * * * *